US012778924B2

(12) United States Patent
Huh et al.

(10) Patent No.: US 12,778,924 B2
(45) Date of Patent: Nov. 3, 2026

(54) PHARMACEUTICAL COMPOSITION FOR PREVENTING OR TREATING DIABETES MELLITUS IN ANIMAL OF FAMILY *CANIDAE*, COMPRISING ENAVOGLIFLOZIN

(71) Applicant: DAEWOONG PHARMACEUTICAL CO., LTD., Hwaseong-si (KR)

(72) Inventors: Wan Huh, Namyangju-si (KR); Hyun Woo Lim, Yongin-si (KR); Ji Soo Choi, Seoul (KR); Ju Mi Han, Seoul (KR); Joon Seok Park, Yongin-si (KR)

(73) Assignee: DAEWOONG PHARMACEUTICAL CO., LTD., Hwaseong-si Gyeonggido (KR)

( * ) Notice: Subject to any disclaimer, the term of this patent is extended or adjusted under 35 U.S.C. 154(b) by 356 days.

(21) Appl. No.: 18/562,428

(22) PCT Filed: May 20, 2022

(86) PCT No.: PCT/KR2022/007206
§ 371 (c)(1),
(2) Date: Nov. 20, 2023

(87) PCT Pub. No.: WO2022/245171
PCT Pub. Date: Nov. 24, 2022

(65) Prior Publication Data

US 2024/0245641 A1 Jul. 25, 2024

(30) Foreign Application Priority Data

May 21, 2021 (KR) ........................ 10-2021-0065733

(51) Int. Cl.
*A61K 31/351* (2006.01)
*A61K 38/28* (2006.01)
*A61P 3/10* (2006.01)

(52) U.S. Cl.
CPC ............ *A61K 31/351* (2013.01); *A61K 38/28* (2013.01); *A61P 3/10* (2018.01)

(58) Field of Classification Search
CPC .......... A61K 31/351; A61K 38/28; A61P 3/10
USPC .......................................................... 514/460
See application file for complete search history.

(56) References Cited

U.S. PATENT DOCUMENTS

| | | | | |
|---|---|---|---|---|
| 9,034,921 | B2 | 5/2015 | Choi et al. | |
| 10,220,017 | B2 | 3/2019 | Weiler et al. | |
| 10,603,300 | B2 * | 3/2020 | Kley ........................ | A61P 1/16 |

FOREIGN PATENT DOCUMENTS

| | | | | |
|---|---|---|---|---|
| JP | 2013536860 | A | 9/2013 | |
| JP | 2020029460 | A | 2/2020 | |
| KR | 20140022086 | A | 2/2014 | |
| KR | 20160108556 | A | 9/2016 | |
| KR | 20180039727 | A | 4/2018 | |
| WO | 2011132990 | A2 | 10/2011 | |
| WO | 2012030968 | A1 | 3/2012 | |
| WO | 2015110402 | A1 | 7/2015 | |
| WO | WO-2021092341 | A1 * | 5/2021 | ................ A61P 9/12 |

OTHER PUBLICATIONS

Daewoong Pharmaceutical, “The Efficacy and Safety of DWP16001 Compared to Placebo in the Treatment of Type 2”, ClinicalTrials.gov, NCT04632862, https://clinicaltrials.gov/study/NCT04632862, Nov. 12, 2020.
Extended European Search Report corresponding to European Patent Application No. 22805024.1 (10 pages) (dated Apr. 9, 2025).
“Daewoong Pharmaceutical Publishes Results of First Clinical Study of SGLT-2 Inhibitor ‘Enavogliflozin’ for Canine Diabetes”, Daewoong Pharmaceutical Co., Ltd (4 pages) (Jun. 1, 2021).
Choi, et al., “Comparative Pharmacokinetics and Pharmacodynamics of a Novel Sodium-Glucose Cotransporter 2 Inhibitor, DWP16001, with Dapagliflozin and Ipragliflozin”, Pharmaceutics, 12:268 (2020).
Hwang, et al., “744 Dose-dependent glucosuria of DWP16001: a novel selective SGLT2 inhibitor in healthy male Korean subjects”, Diabetologia, 62(Suppl. 1):S358 (2019).
Hwang, et al., “Dose-dependent glucosuria of DWP16001, a novel selective sodium-glucose cotransporter-2 inhibitor, in healthy subjects”, British Journal of Clinical Pharmacology, 88:4100-4110 (2022).
Kim, et al., “In Vitro Metabolism of DWP16001, a Novel Sodium-Glucose Cotransporter 2 Inhibitor, in Human and Animal Hepatocytes”, Pharmaceutics, 12:865 (2020).
Paszkiewicz, et al., “Dapagliflozin Improves Insulin Sensitivity in the Obese Prediabetic Canine”, Diabetes, 67 (Supplement 1):113-LB (2018).
Xu, et al., “Design, synthesis, and biological evaluation of deuterated C-Aryl glycoside as a potent and long-acting renal sodium-dependent glucose cotransporter 2 inhibitor for the treatment of type 2 diabetes”, Journal of Medicinal Chemistry, 57:1236-1251 (2014).
Yamamoto, et al., “TS-071 is a novel, potent and selective renal sodium-glucose cotransporter 2 (SGLT2) inhibitor with anti-hyperglycaemic activity”, British Journal of Pharmacology, 164:181-191 (2011).
English translation of International Search Report corresponding to International Patent Application No. PCT/ KR2022/007206 (3 pages) (mailed Aug. 26, 2022).

* cited by examiner

*Primary Examiner* — Yevgeny Valenrod
(74) *Attorney, Agent, or Firm* — Myers Bigel, P.A.

(57) ABSTRACT

The present invention relates to a pharmaceutical composition for preventing or treating diabetes mellitus in an animal of the family Canidae, including enavogliflozin as an active ingredient. The pharmaceutical composition, of the present invention, including enavogliflozin as an active ingredient exhibits an excellent blood glucose level control effect and thus can be effectively used for treating diabetes mellitus in an animal of the family Canidae.

9 Claims, 8 Drawing Sheets

【FIG. 1A】
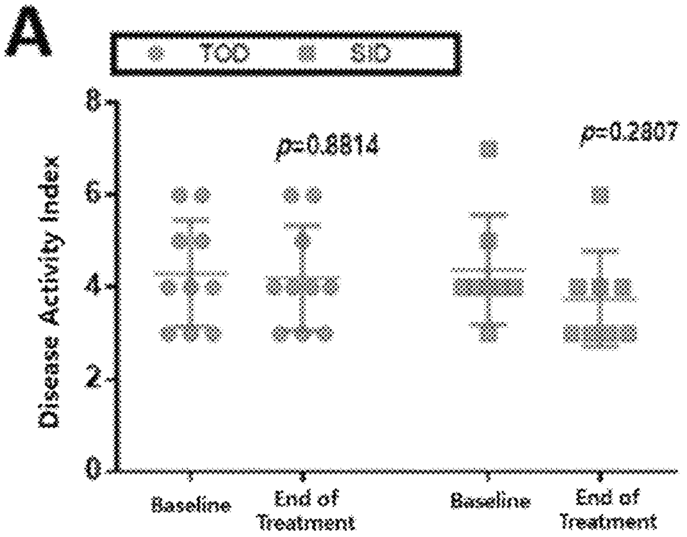
【FIG. 1B】
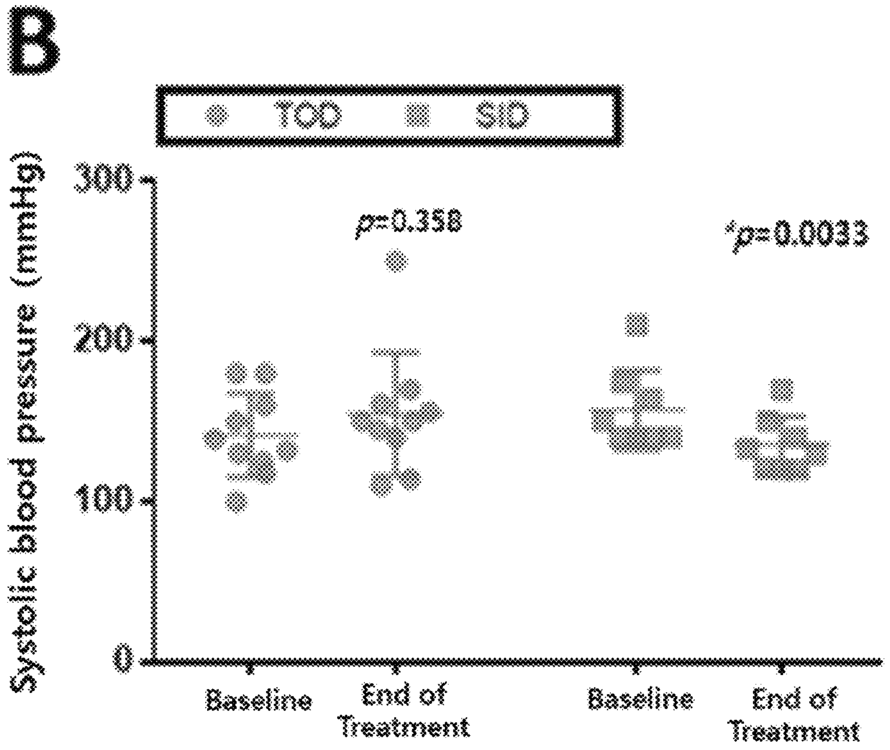

【FIG. 1C】
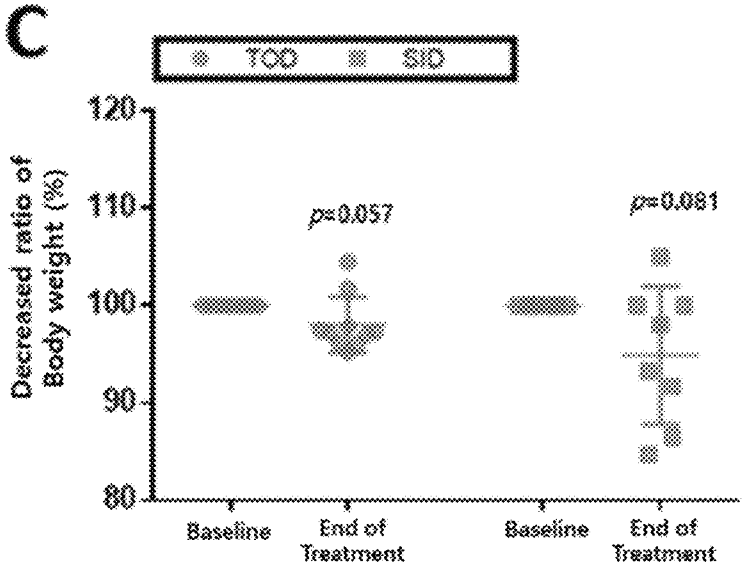
【FIG. 1D】
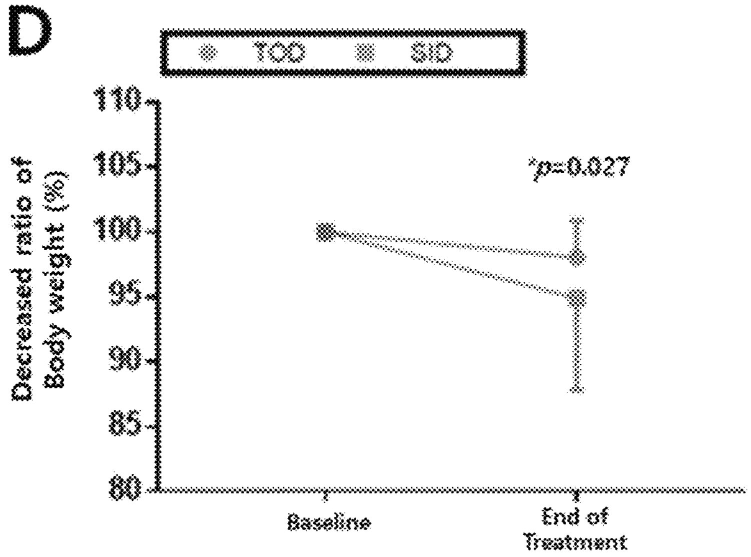

【FIG. 2A】
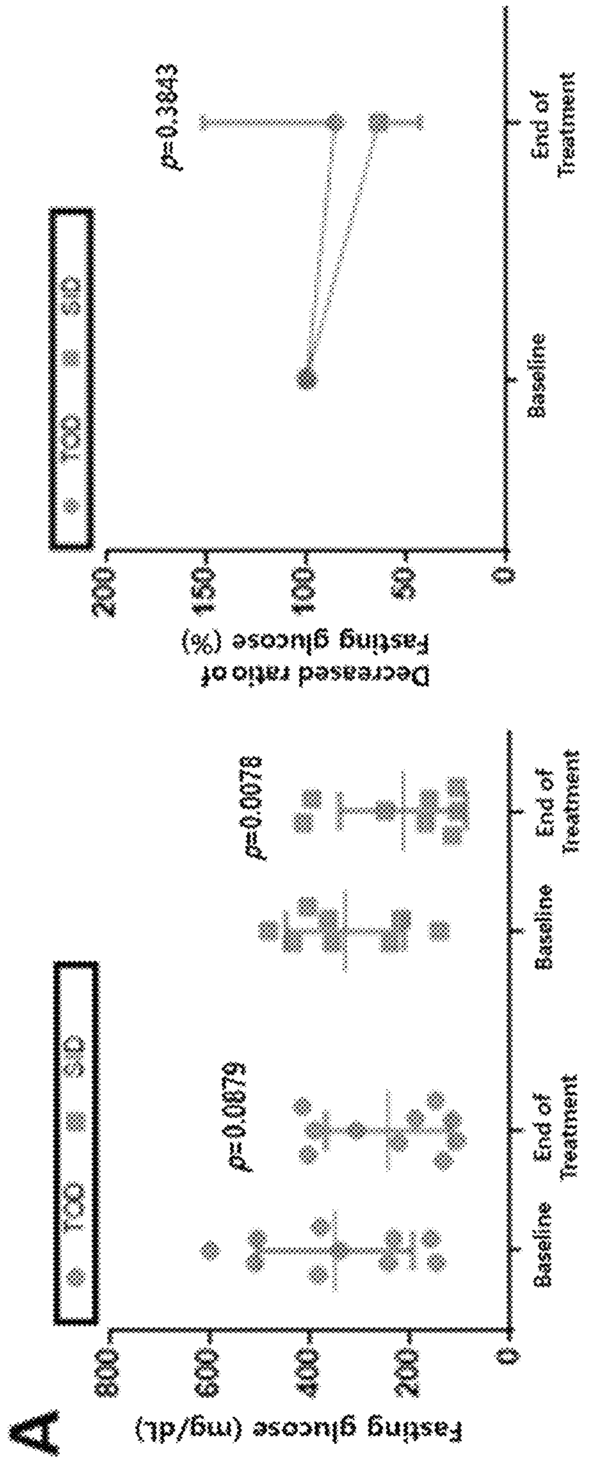

【FIG. 2B】
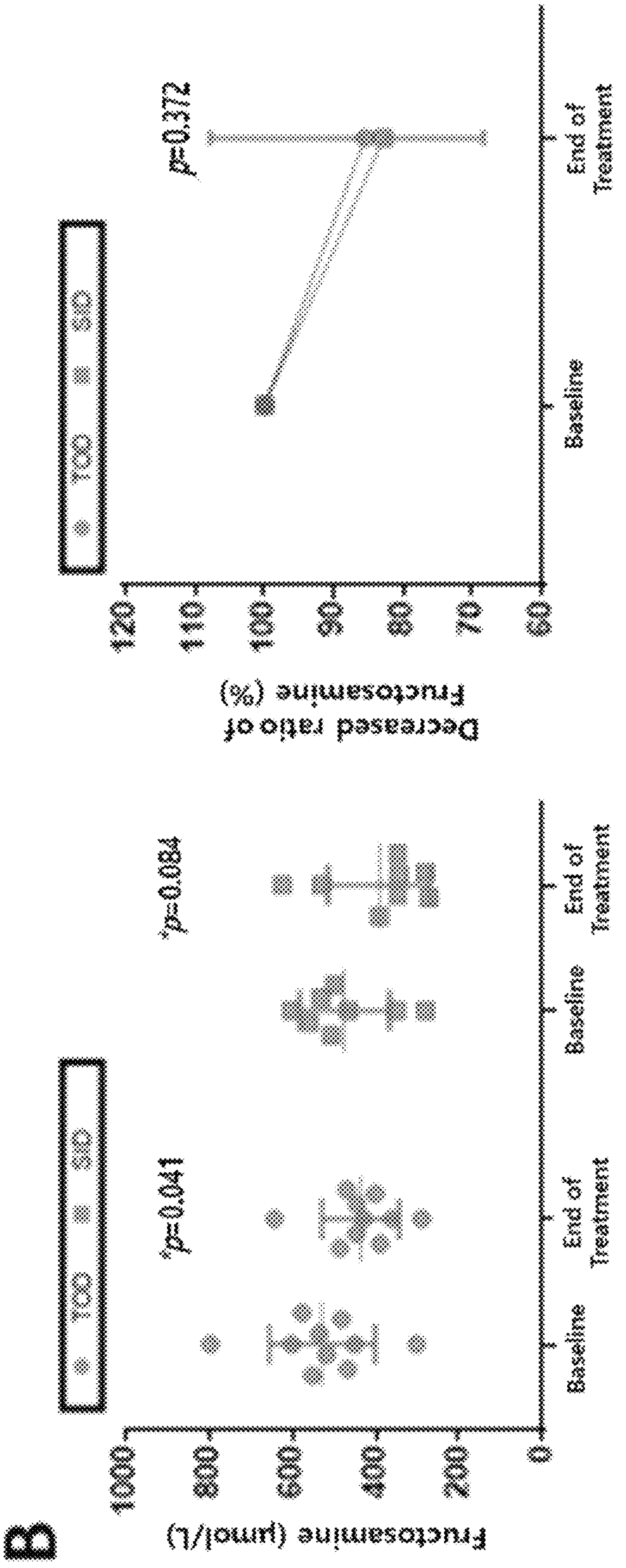

【FIG. 2C】
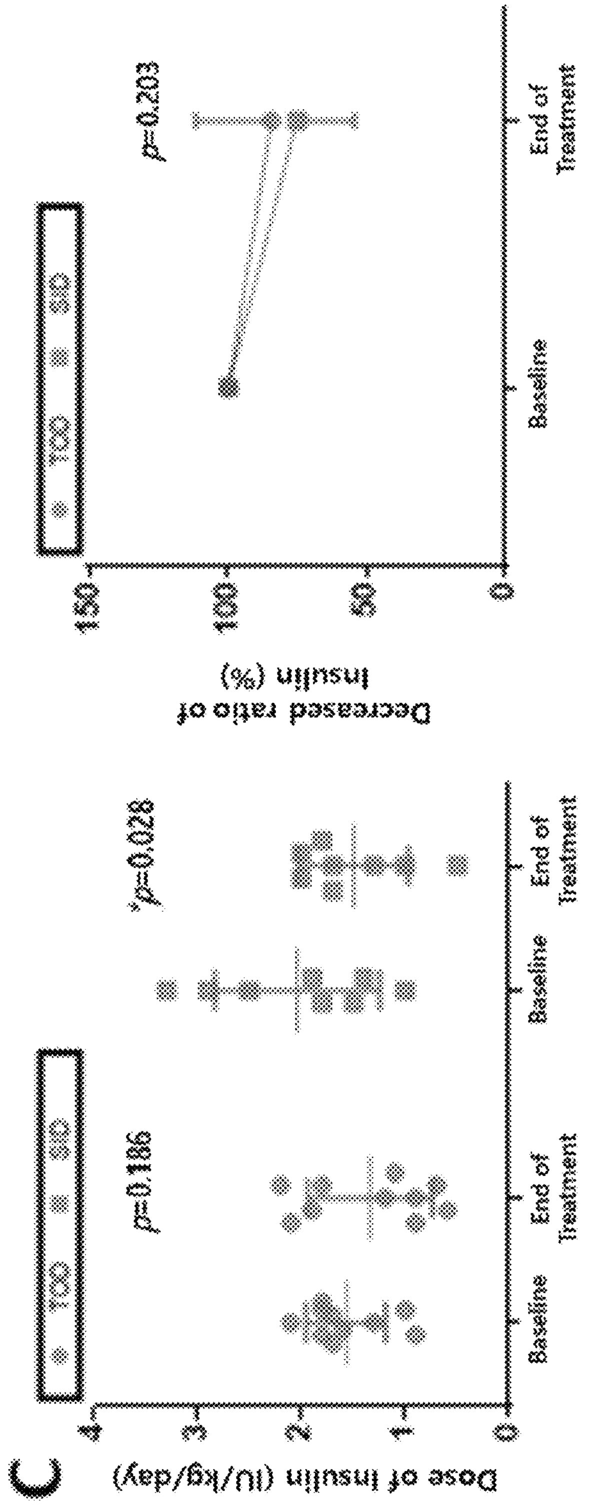

【FIG. 3A】
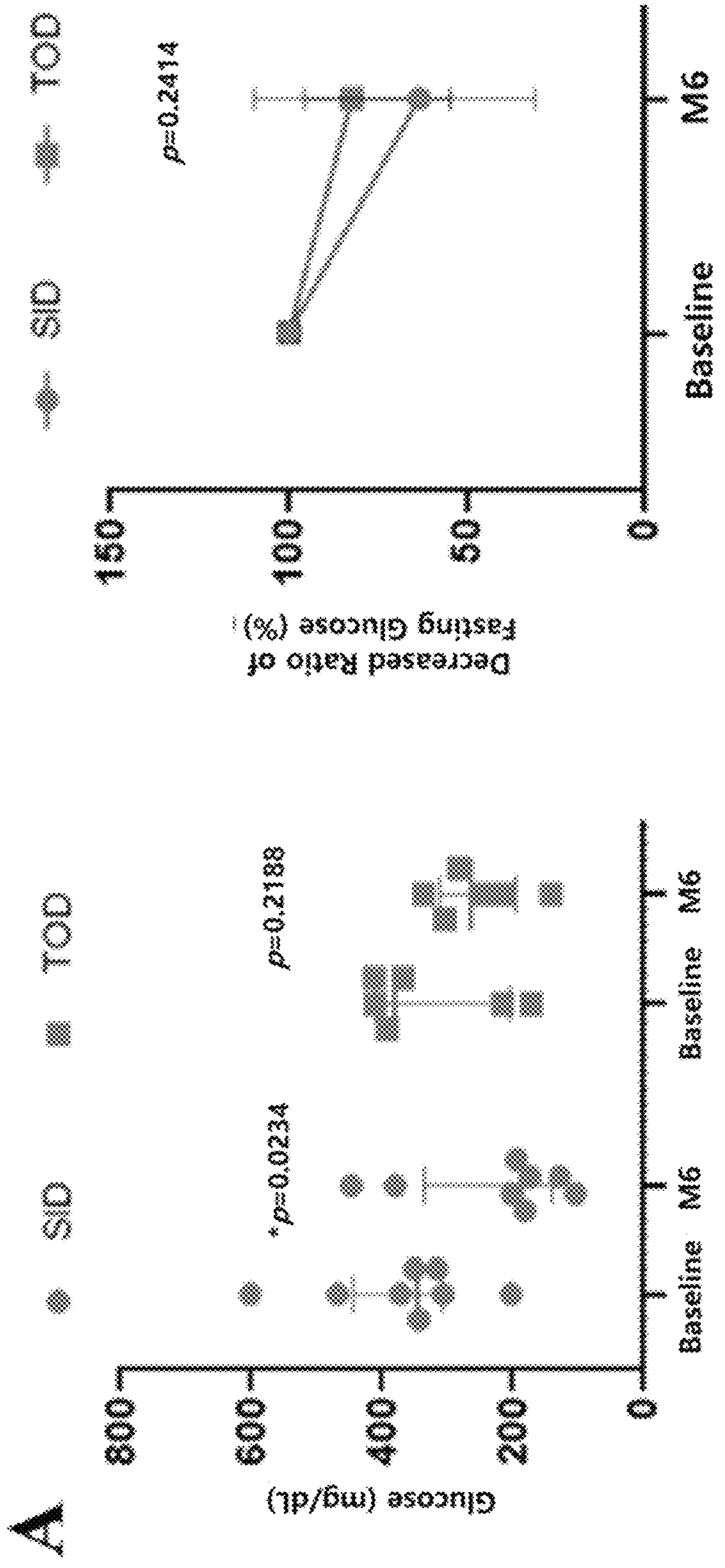

【FIG. 3B】
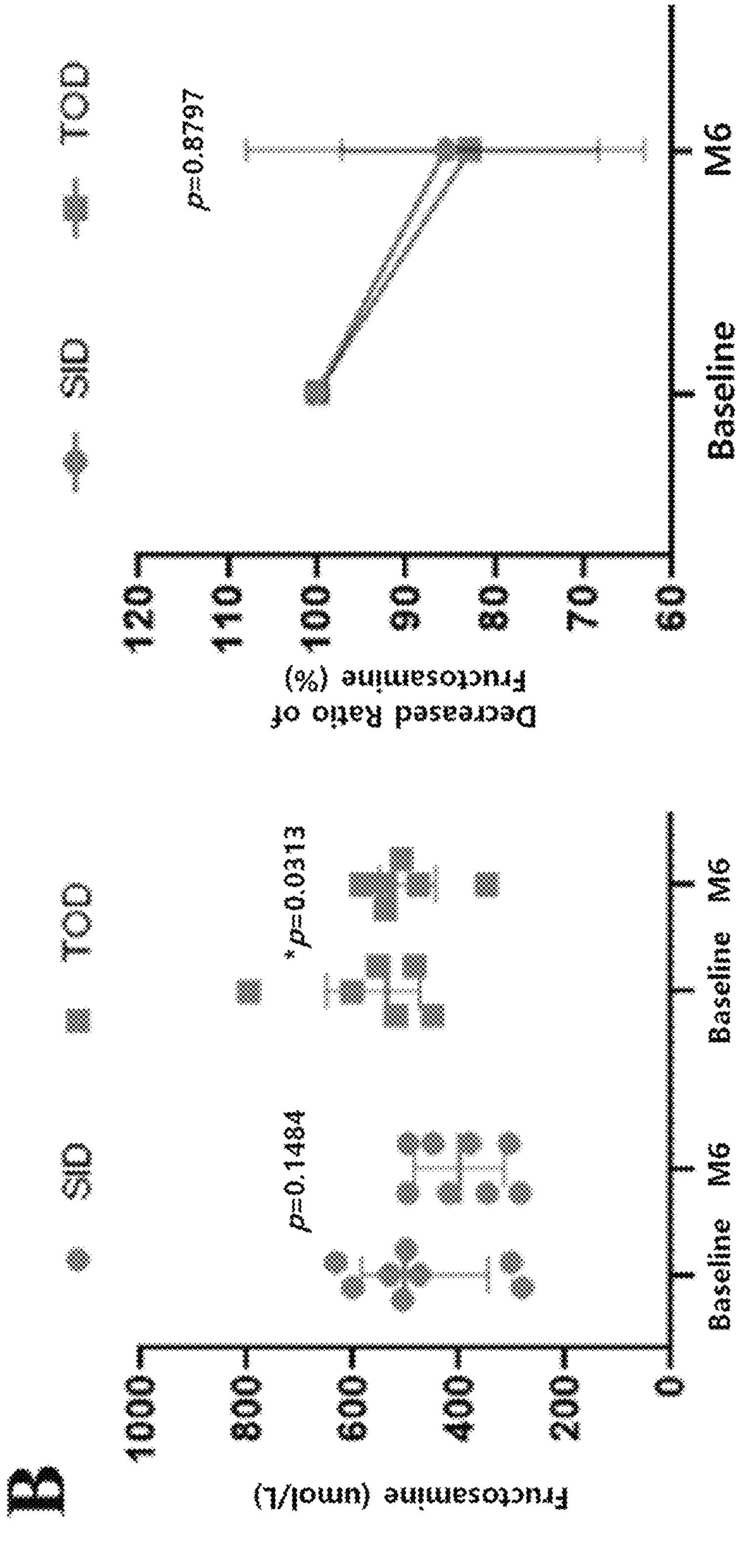

【FIG. 3C】
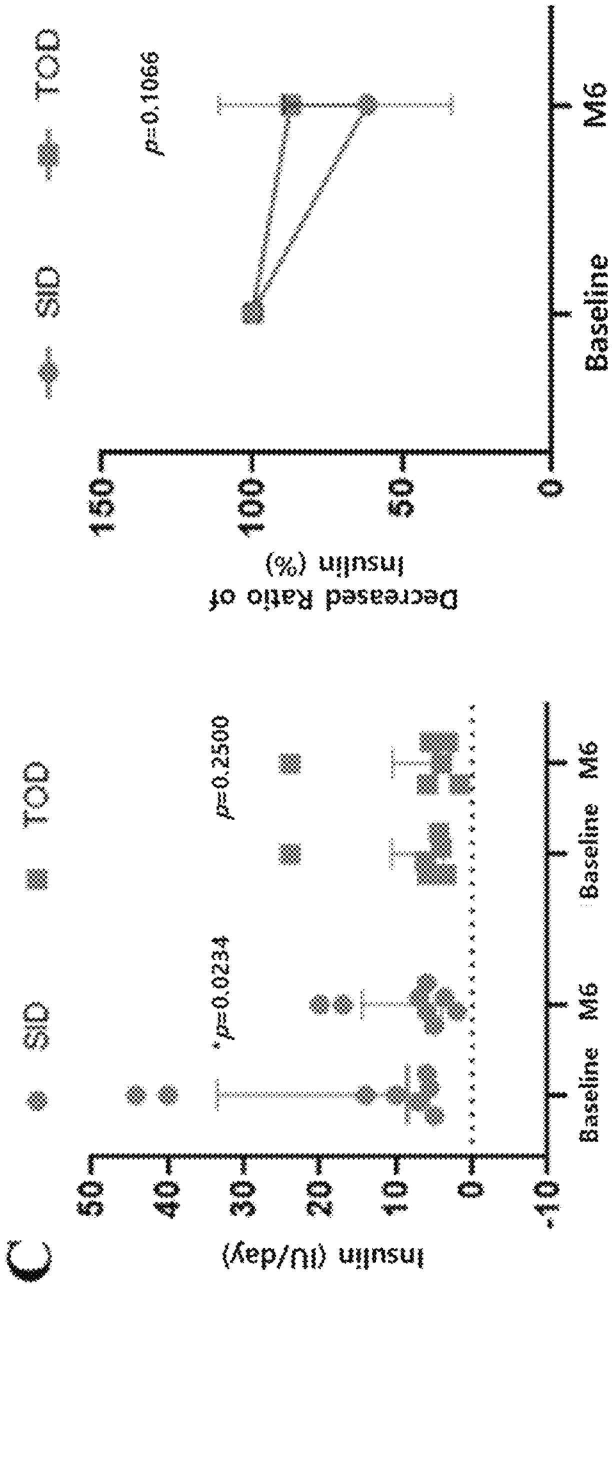

PHARMACEUTICAL COMPOSITION FOR PREVENTING OR TREATING DIABETES MELLITUS IN ANIMAL OF FAMILY *CANIDAE*, COMPRISING ENAVOGLIFLOZIN

TECHNICAL FIELD

The present invention relates to a pharmaceutical composition for preventing or treating diabetes mellitus in an animal of the family Canidae, including enavogliflozin as an active ingredient.

BACKGROUND ART

Diabetes mellitus (DM) is one of the common metabolic disorders affecting middle-aged and elderly dogs and is characterized by body weight loss due to hyperglycemia, glycosuria, and absolute or relative deficiency of insulin.

As the number of people who keep companion dogs is rapidly increasing, more and more households are paying attention to the health of their companion dogs. Skin diseases, eczema, and the like are common in companion dogs, but diabetes mellitus, heart disease, kidney disease and cancer increase with age. In particular, when a companion dog shows symptoms of polydipsia and polyuria and loses body weight rapidly, diabetes mellitus should be suspected. Unlike people who are more likely to have non-insulin-dependent diabetes mellitus (type 2 diabetes mellitus) due to obesity and lack of exercise, almost all diabetic dogs suffer from insulin-dependent diabetes mellitus (type 1 diabetes mellitus).

Although insulin therapy is still the main treatment method for diabetic dogs, it is difficult to strictly control diabetes mellitus due to the inconvenience of having to take insulin injections several times a day and the limited dose caused by hypoglycemia. Consequently, there is an unmet need for insulin and adjunctive therapy to solve the dual problems of hyperglycemia and hypoglycemia.

Meanwhile, sodium-glucose cotransporter 2 (SGLT2) inhibitors are a new class of antihyperglycemic agents. SGLT-2 inhibitors reduce glucose reabsorption in the proximal nephron and increase glucose excretion through a mechanism independent of insulin, and the safety and efficacy of SGLT2 inhibitors for the treatment of type 2 diabetes mellitus have been confirmed in numerous studies. In particular, U.S. Patent Publication No. 2015/0152075 discloses enavogliflozin as a compound having a diphenylmethane moiety that exhibits inhibitory activity against SGLT2, and the document discloses that enavogliflozin has an excellent inhibitory effect on human SGLT2 activity and thus is effective for treating diabetes mellitus.

DISCLOSURE

Technical Problem

As a result of administering enavogliflozin to diabetic dogs in order to solve the problem that there is no appropriate treatment method other than insulin injection in the treatment of diabetic dogs, the present inventors confirmed that enavogliflozin has an excellent blood glucose regulating effect, thereby completing the present invention.

Therefore, an object of the present invention is to provide a pharmaceutical composition for preventing or treating diabetes mellitus in an animal of the family Canidae, including enavogliflozin as an active ingredient.

Technical Solution

As described above, diabetes mellitus in an animal of the family Canidae is characterized by metabolic disorders such as hyperglycemia, insulin deficiency, and body weight loss. This corresponds to type 1 diabetes mellitus in humans and has been treated mainly through insulin injections.

The clinical symptoms of diabetes mellitus are polydipsia, polyuria and polyphagia. While the normal water intake for an animal of the family Canidae is 50 ml/kg, the water intake for an animal of the family Canidae suffering from diabetes mellitus may increase to 100 ml/kg or more. An animal of the family Canidae suffering from diabetes mellitus may have complications such as diabetic cataracts, uveitis, and ketoacidosis.

Diabetes mellitus is diagnosed by comprehensively judging the results of clinical symptoms, a blood glucose check, urinary glucose detection, a fructosamine level test, and the like as described above.

As confirmed in the following examples, enavogliflozin showed effects of reducing blood glucose levels, improving fructosamine concentrations, reducing the required daily dose of insulin, and lowering systolic blood pressure in dogs suffering from diabetes mellitus.

Therefore, the present invention provides a pharmaceutical composition for preventing or treating diabetes mellitus in an animal of the family Canidae, including enavogliflozin as an active ingredient.

A representative example of the animal of the family Canidae is a dog. In addition to a dog, a fox, a wolf, a raccoon, and the like are included in the animals of the family Canidae.

As used herein, the term "prevention" refers to all actions that suppress the onset of diabetes mellitus or delay the onset of diabetes mellitus by administering the pharmaceutical composition according to the present invention.

Further, as used herein, the term "treatment" refers to all actions that ameliorate or beneficially change symptoms of diabetes mellitus by administering the pharmaceutical composition according to the present invention. More specifically, the treatment may be determined by reducing fructosamine concentration or fasting blood glucose, which is a blood glucose control index, or body fat, and the like.

In an exemplary embodiment of the invention, the diabetes mellitus may be insulin dependent diabetes mellitus, that is, type 1 diabetes mellitus. Type 1 diabetes mellitus occurs due to the lack of insulin production in the pancreas, and is caused by the destruction or loss of pancreatic beta cells. There is still no effective therapeutic method other than direct injection of insulin. Meanwhile, diabetes mellitus is prone to complications due to elevated blood glucose levels, so the animal of the family Canidae may have complications such as, but not limited to, diabetes mellitus, as well as diabetic cataracts, uveitis, and ketoacidosis.

The dose of enavogliflozin that can be used for the prevention or treatment of diabetes mellitus in an animal of the family Canidae is not particularly limited, and can be appropriately adjusted according to the severity of the disease, body weight, age, sex, and presence or absence of complications of the animal of the family Canidae subject to administration.

In an exemplary embodiment of the present invention, the enavogliflozin may be administered at a dose of 0.01 to 0.1 mg/kg, for example, 0.01 to 0.08 mg/kg, 0.01 to 0.05 mg/kg, and 0.02 to 0.05 mg/kg once a day, but the dose is not limited thereto. In an exemplary embodiment of the present invention, the enavogliflozin may be administered at a dose of 0.02 to 0.03 mg/kg once a day. Alternatively, the enavogliflozin may be administered at a dose of 0.01 to 0.1 mg/kg, for example, 0.01 to 0.08 mg/kg, 0.01 to 0.05 mg/kg, and 0.02 to 0.05 mg/kg once every three days. For example, enavogliflozin may be administered at a dose of 0.02 to 0.03 mg/kg once every three days.

In the following examples, the present inventors administered enavogliflozin at a dose of 0.025 mg/kg along with insulin to a diabetic dog once every three days or once a day for eight weeks. As a result, it was confirmed that systolic blood pressure was further reduced in the diabetic dog when enavogliflozin was administered once a day than when enavogliflozin was administered once every three days (FIG. 1B), and fructosamine, fasting blood glucose and insulin dose were also remarkably reduced (FIG. 2). In addition, as a result of administration at the same usage and dose for 6 months, it was confirmed that fasting blood glucose and insulin dose decreased statistically significantly when administered once a day (FIG. 3). Through these results, the present invention demonstrated that the frequency of administration of enavogliflozin in the treatment of a diabetic dog, that is, once-a-day administration elicits the optimal effect, and enavogliflozin is safe even though it is administered for a long period of time.

The duration of administration of enavogliflozin can be appropriately adjusted by a clinician based on the preventive or therapeutic effect of diabetes mellitus in an animal of the family Canidae according to the administration of enavogliflozin. A pharmaceutical composition including enavogliflozin as an active ingredient may be administered once a day for at least 8 weeks and at least 6 months for the prevention or treatment of diabetes mellitus in an animal of the family Canidae, but the duration of administration is not limited thereto. In addition, the pharmaceutical composition may be administered for at least 8 weeks to 6 months.

The administration of the pharmaceutical composition exhibits an effect of reducing one or more indices selected from the group consisting of fructosamine, fasting blood glucose and systolic blood pressure.

In an exemplary embodiment, the diabetes mellitus is type 1 diabetes mellitus, and the pharmaceutical composition of the present invention may be administered in combination with a therapeutic agent for type 1 diabetes mellitus. For example, the therapeutic agent for type 1 diabetes mellitus may be insulin. As can be confirmed in the following examples, the administration of a pharmaceutical composition including enavogliflozin exhibits an effect of remarkably reducing the insulin dose in an animal of the family Canidae, thereby providing a therapeutically significant advantage.

Meanwhile, the method of administering the pharmaceutical composition including enavogliflozin according to the present invention is not limited thereto, but the pharmaceutical composition may be administered orally or parenterally according to a desired method. Preparations for oral administration may be selected from various forms such as syrups, tablets, capsules, creams and lozenges. A syrup preparation will generally contain a suspension or solution of a compound, or a salt thereof, in a liquid carrier optionally including a flavoring or coloring agent, for example, ethanol, peanut oil, olive oil, glycerin or water. When the composition is present in the form of a tablet, any one of the pharmaceutical carriers commonly used for preparing a solid preparation may be used. Examples of such carriers include magnesium stearate, terra alba, talc, gelatin, acacia, stearic acid, starch, lactose and sucrose. When the composition is present in the form of a capsule, one of the general encapsulation procedures may be used, for example, using the above-mentioned carrier in a hard gelatin capsule shell. When the composition is prepared in the form of a soft gelatin shell capsule, any one of the pharmaceutical compositions commonly used in dispersions or suspensions may be prepared using an aqueous gum, cellulose, silicate or oil. Preparations for intramuscular or subcutaneous administration may be in the form of a liquid, for example, a solution including an aqueous solvent such as water, physiological saline and Ringer's solution, or a lipophilic solvent such as fatty oils, sesame oil, corn oil and synthetic fatty acid esters, a suspension and an emulsion may be selected.

The present invention also provides a method for treating diabetes mellitus in an animal of the family Canidae, the method including administering the pharmaceutical composition including enavogliflozin as an active ingredient to an animal of the family Canidae in need of treatment.

The animal of the family Canidae in need of treatment may have, but is not limited to, a metabolic disorder selected from the group consisting of hyperglycemia, insulin deficiency and body weight loss.

In an exemplary embodiment of the present invention, the treatment method may be the administration of a pharmaceutical composition for preventing or treating diabetes mellitus in combination with insulin.

Since a pharmaceutical composition for prevention or treating diabetes mellitus is used in the method for treating diabetes mellitus, descriptions of overlapping contents between the two will be omitted to avoid excessive description in the specification.

Advantageous Effects

The pharmaceutical composition of the present invention for preventing or treating diabetes mellitus in an animal of the family Canidae, including enavogliflozin as an active ingredient exhibits an excellent blood glucose level control effect and thus can be effectively used for treating diabetes mellitus in an animal of the family Canidae.

DESCRIPTION OF DRAWINGS

FIG. 1A shows the disease activity index after co-administration of insulin and enavogliflozin to diabetic dogs: TOD is a test group to which enavogliflozin is administered at a dose of 0.025 mg/kg once every 3 days, and SID is a test group to which enavogliflozin is administered at a dose of 0.025 mg/kg once a day. Bar graphs represent the mean for each variable, error bars represent S.D, and p-values less than 0.05 were considered statistically significant.

FIG. 1B shows the systolic blood pressure after co-administration of insulin and enavogliflozin to diabetic dogs: TOD is a test group to which enavogliflozin is administered at a dose of 0.025 mg/kg once every 3 days, and SID is a test group to which enavogliflozin is administered at a dose of 0.025 mg/kg once a day. Bar graphs represent the mean for each variable, error bars represent S.D, and p-values less than 0.05 were considered statistically significant.

FIG. 1C shows the results of confirming the degree of body weight loss after co-administration of insulin and enavogliflozin to diabetic dogs: TOD is a test group to which enavogliflozin is administered at a dose of 0.025 mg/kg once every 3 days, and SID is a test group to which enavogliflozin is administered at a dose of 0.025 mg/kg once a day. Bar graphs represent the mean for each variable, error bars represent S.D, and p-values less than 0.05 were considered statistically significant.

FIG. 1D shows the results of confirming the degree of body weight loss after co-administration of insulin and enavogliflozin to diabetic dogs: TOD is a test group to which enavogliflozin is administered at a dose of 0.025 mg/kg once every 3 days, and SID is a test group to which enavogliflozin is administered at a dose of 0.025 mg/kg once a day. Bar graphs represent the mean for each variable, error bars represent S.D, and p-values less than 0.05 were considered statistically significant.

FIG. 2A shows the results of confirming fasting blood glucose after co-administration of insulin and enavogliflozin to diabetic dogs: TOD is a test group to which enavogliflozin is administered at a dose of 0.025 mg/kg once every 3 days, and SID is a test group to which enavogliflozin is administered at a dose of 0.025 mg/kg once a day. Bar graphs represent the mean for each variable, error bars represent S.D, and p-values less than 0.05 were considered statistically significant.

FIG. 2B shows the results of confirming a fructosamine concentration after co-administration of insulin and enavogliflozin to diabetic dogs: TOD is a test group to which enavogliflozin is administered at a dose of 0.025 mg/kg once every 3 days, and SID is a test group to which enavogliflozin is administered at a dose of 0.025 mg/kg once a day. Bar graphs represent the mean for each variable, error bars represent S.D, and p-values less than 0.05 were considered statistically significant.

FIG. 2C shows the results of confirming the insulin dose after co-administration of insulin and enavogliflozin to diabetic dogs: TOD is a test group to which enavogliflozin is administered at a dose of 0.025 mg/kg once every 3 days, and SID is a test group to which enavogliflozin is administered at a dose of 0.025 mg/kg once a day. Bar graphs represent the mean for each variable, error bars represent S.D, and p-values less than 0.05 were considered statistically significant.

FIG. 3A shows the results of confirming fasting blood glucose after co-administration of insulin and enavogliflozin to diabetic dogs for 6 months: TOD is a test group to which enavogliflozin is administered at a dose of 0.025 mg/kg once every 3 days, and SID is a test group to which enavogliflozin is administered at a dose of 0.025 mg/kg once a day. Bar graphs represent the mean for each variable, error bars represent S.D, and p-values less than 0.05 were considered statistically significant.

FIG. 3B shows the results of confirming a fructosamine concentration after co-administration of insulin and enavogliflozin to diabetic dogs for 6 months: TOD is a test group to which enavogliflozin is administered at a dose of 0.025 mg/kg once every 3 days, and SID is a test group to which enavogliflozin is administered at a dose of 0.025 mg/kg once a day. Bar graphs represent the mean for each variable, error bars represent S.D, and p-values less than 0.05 were considered statistically significant.

FIG. 3C shows the results of confirming the insulin dose after co-administration of insulin and enavogliflozin to diabetic dogs for 6 months: TOD is a test group to which enavogliflozin is administered at a dose of 0.025 mg/kg once every 3 days, and SID is a test group to which enavogliflozin is administered at a dose of 0.025 mg/kg once a day. Bar graphs represent the mean for each variable, error bars represent S.D, and p-values less than 0.05 were considered statistically significant.

MODES OF THE INVENTION

Hereinafter, one or more specific exemplary embodiments will be described in more detail through examples. However, these examples are provided only for exemplarily explaining the one or more specific exemplary embodiments, and the scope of the present invention is not limited to these examples.

Experimental Method

1. Research Design

This study evaluated the safety and efficacy of enavogliflozin along with insulin therapy in dogs with insulin-dependent diabetes mellitus (type 1 diabetes mellitus) as a prospective, open-label, non-randomized, multicenter, and proof-of-concept study. The efficacy and safety of enavogliflozin were evaluated at predetermined times during the treatment period.

2. Drug Information

Enavogliflozin has the following Chemical Formula 1 and is currently under development as a therapeutic agent for diabetes mellitus through selective inhibition of sodium-glucose cotransporter 2.

[Chemical Formula 1]

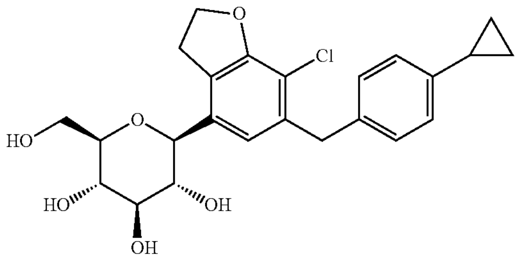

3. Dogs Participating in Clinical Trial

Diabetic dogs meeting the following criteria were allowed to participate in a clinical trial: Small dogs under 15 years of age (less than 10 kg), medium-sized dogs under 13 years of age (11 to 22 kg), stable basal dose insulin therapy at least 1 month prior to the screening visit, post-insulin nadir (Nadir) blood glucose minimum of 200 mg/dl, and blood ketone levels less than 0.6 mmol/L.

However, diabetic dogs meeting the following criteria were excluded: Dogs with chronic kidney disease (CKD IRIS stage >2), hypotension evaluation, administration of diuretics or related drugs, confirmed pregnancy, and taking drugs affecting the test within 14 days prior to test start.

4. Research Process

The study was performed for 8 weeks, and dogs participating in the clinical trial were divided into two groups, a TOD test group and a SID test group, according to the dose of enavogliflozin administered. Enavogliflozin was administered to the TOD test group and the SID test group at a dose of 0.025 mg/kg once every 3 days and once a day, respectively. For proper evaluation, the dogs were administered the drug with breakfast, and after dosing was completed, dogs underwent physical examinations such as blood pressure, blood tests and urine tests. Thereafter, researchers adjusted insulin doses to meet target blood glucose levels during monitoring (Nadir glucose levels, 80 to 150 mg/dl).

A primary evaluation variable was whether blood fructosamine levels decreased without developing severe hypoglycemia or diabetic ketoacidosis (DKA) after the animals were randomly divided into groups. A secondary evaluation variable was a change in fasting blood glucose levels, body weight and a mean bolus dose of insulin from baseline to 8 weeks. Severe hypoglycemia was defined as a hypoglycemic condition in which a dog required help or lost consciousness or had a seizure, regardless of the glucose level of a dog. The diagnosis of diabetic ketoacidosis was evaluated based on the presence of anion-gap metabolic acidosis associated with excessive ketogenesis without other causes. Safety information including data on clinical and laboratory values and side effects was collected at each study visit.

In addition, long-term effectiveness was confirmed by additionally administering enavogliflozin to the companion dogs participating in the clinical trial at the same usage and dosage (SID or TOD) for up to 6 months.

5. Statistical Analysis

Differences before and after drug administration within the groups were compared using the Student paired t-test or the Wilcoxon rank test. Furthermore, differences between groups after drug administration through a mixed ANOVA test were confirmed. Statistical analysis was performed with the R programming language (https://cran.r-project.org/) and GraphPad Prism version 7 (GraphPad Software, Inc., La Jolla, California). A p-value less than 0.05 was considered statistically significant.

Experimental Results

11. Characteristics of Dogs Participating in Clinical Trial

Eighteen dogs participating in the clinical trial were divided into two test groups (TOD and SID test groups) according to the administration dose of enavogliflozin, and the sex, age, and body condition score (BCS) and systolic blood pressure distribution of the participating dogs for each group are shown in Table 1. In Table 1, age and BCS are indicated as median values along with ranges, and systolic blood pressure and insulin dose values are expressed as mean±SD.

TABLE 1

| | Reference | Test group | |
|---|---|---|---|
| Parameter | Range | TOD (n = 10) | SID (n = 8) |
| Sex | NA | CM (5), SF (2), F (1), Unknown (2) | CM (5), SF (1), F (1), Unknown (1) |
| Age (years old) | NA | 12 (5-16) | 10.5 (8-15) |
| BCS | NA | 4 (4-6) | 5 (3-7) |
| Systolic blood pressure (mmHg) | <140 | 141.8 ± 20.5 | 157.3 ± 24.9 |
| Insulin dose (IU/kg/day) | NA | 1.6 ± 0.4 | 2.0 ± 0.8 |

2. Evaluation of Side Effects after Administration of Enavogliflozin

It was confirmed whether there were side effects by checking appetite, activity, and stool status after administration of enavogliflozin. As a result of confirming the disease activity index in Table 2, it was confirmed that there was no difference between before and after administration in each test group.

TABLE 2

| Score | Appetite | Activity | Stoll status |
|---|---|---|---|
| 1 | All intake of any type | Very energetic and active | Normal stool |
| 2 | Leave the food don't like | Good vitality | Hard and dry stool |
| 3 | Less than ¾ of the usual intake | Normal vitality | Soft stool |
| 4 | Less than ½ of the usual intake | Lack of energy | Shapeless stool |
| 5 | Don't eat favorite food | Loss of energy and slow motion | Liquid stool |

At the start of the experiment, it was confirmed that two animals in the TOD test group and one animal in the SID test group were suffering from bacterial cystitis, but after the administration of enavogliflozin, one of the two animals in the TOD test group completely recovered from cystitis, and one animal in the SID test group had no amelioration of cystitis even after the end of the clinical trial. However, there were no new cases of bacterial cystitis in any test group.

There was no severe hypoglycemia leading to loss of consciousness or seizures in any test group.

3. Evaluation of Body Weight and Blood Pressure after Administration of Enavogliflozin Changes in body weight and blood pressure after administration of enavogliflozin were also confirmed. Body weight tended to decrease in both groups, and there was no difference in BCS. Blood pressure was significantly reduced in the SID test group (p=0.033) (FIG. 1B).

4. Evaluation of Renal Function after Administration of Enavogliflozin

Changes in renal function before and after administration of enavogliflozin were confirmed through blood and urine tests. Blood test items include blood urea nitrogen (BUN), creatinine, symmetric di-methyl-arginine (SDMA), cystatin-C, beta-2-microglobulin (B2M) and N-acetyl-β-d-glucosaminidase (NAG). Urinalysis items include urine specific gravity (USG) and urine protein to creatinine (UPC) ratio.

In the TOD test group, there were no significant changes in BUN (21.3±11.7 to 22.5±11.7, p=0.723), creatinine (0.9±0.2 to 0.9±0.2, p=0.733), SDMA (8.8±2.9 to 9.2±5.5, p=0.943), cystatin-C (0.6±0.3 to 0.5±0.2, p=0.082), NAG (7.0±8.3 to 7.6±5.8, p=0.293), USG (1.032±0.016 to 1.034±0.011, p=1) and UPC (1.9±3.0 to 1.1±1.8, p=0.185) before and after administration of enavogliflozin.

In the SID test group, there were no significant changes in creatinine (0.6±0.1 to 0.6±0.1, p=0.316), SDMA (8.9±2.6 to 7.8±1.4, p=0.124), cystatin-C (0.5±0.1 to 0.5±0.1, p=0.335), NAG (11.0±7.3 to 9.0±4.3, p=0.293), USG (1.035±0.016 to 1.043±0.008, p=0.16) and UPC (1.2±2.2 to 1.1±1.6, p=0.779) before and after administration of enavogliflozin. However, in the case of BUN, a significant increase could be confirmed after administration (15.2±4.9 to 21.9±6.8, p=0.003). Beta-2-microglobulin (B2M) concentrations were shown to be less than 0.16 before and after administration in both the test groups (Table 3). In Table 3, all values are expressed as mean±S.D, and p-values less than 0.05 were considered statistically significant.

TABLE 3

| | Reference | TOD test group (n = 10) | | | SID test group (n = 8) | | |
|---|---|---|---|---|---|---|---|
| Parameter | range | basal | treatment | p-value | basal | treatment | p-value |
| BUN (mg/dL) | 5-30 | 21.3 ± 11.7 | 22.5 ± 11.7 | 0.723 | 15.2 ± 4.9 | 21.9 ± 6.8 | *0.003 |
| Creatinine (mg/dL) | 0.5-1.5 | 0.9 ± 0.2 | 0.9 ± 0.2 | 0.733 | 0.6 ± 0.1 | 0.6 ± 0.1 | 0.316 |
| SDMA (μg/dL) | <14 | 8.8 ± 2.9 | 9.2 ± 5.5 | 0.943 | 8.9 ± 2.6 | 7.8 ± 1.4 | 0.124 |
| Cystatin-C (mg/L) | NA | 0.6 ± 0.3 | 0.5 ± 0.2 | 0.082 | 0.5 ± 0.1 | 0.5 ± 0.1 | 0.335 |
| NAG (U/g) | NA | 7.0 ± 8.3 | 7.6 ± 5.8 | 0.4755 | 11.0 ± 7.3 | 9.0 ± 4.3 | 0.293 |
| B2M (mg/dL) | NA | <0.16 | <0.16 | — | <0.16 | <0.16 | — |
| USG | NA | 1.032 ± 0.016 | 1.034 ± 0.011 | 1 | 1.035 ± 0.016 | 1.043 ± 0.008 | 0.16 |
| UPC | ≤0.5 | 1.9 ± 3.0 | 1.1 ± 1.8 | 0.185 | 1.2 ± 2.2 | 1.1 ± 1.6 | 0.779 |

5. Evaluation of Metabolic Acidosis after Administration of Enavogliflozin

Eight weeks after administration of enavogliflozin, changes in blood ketones were confirmed, and an increasing trend was observed in the SID test group, but the increase was not significant. In addition, when lactate dehydrogenase (LDH) was measured, there was no significant change in both test groups compared to before administration. Blood pH, bicarbonate ($HCO_3$), and the anion gap were confirmed by a venous blood gas test, and there was no significant difference before and after administration (Table 4). As a result, it was confirmed that diabetic ketoacidosis did not occur. In Table 4, all values are expressed as mean±S.D, and p-values less than 0.05 were considered statistically significant.

TABLE 4

| | Reference | TOD test group (n = 10) | | | SID test group (n = 8) | | |
|---|---|---|---|---|---|---|---|
| Parameter | range | basal | treatment | p-value | basal | treatment | p-value |
| Ketone (mmol/L) | 0.3-0.6 | 0.2 ± 0.1 | 0.2 ± 0.1 | 0.2325 | 0.3 ± 0.1 | 0.4 ± 0.1 | 0.0567 |
| LDH (U/L) | 65-269 | 435.6 ± 412.1 | 444.5 ± 584.7 | 0.475 | 383.2 ± 443.0 | 230.8 ± 79.6 | 1 |
| pH | 7.35-7.45 | 7.4 ± 0.1 | 7.4 ± 0.1 | 0.08 | 7.4 ± 0.1 | 7.4 ± 0.1 | 0.38 |
| $HCO_3$ (mmol/L) | 17-28 | 22.8 ± 4.2 | 24.3 ± 3.6 | 0.265 | 24.9 ± 3.2 | 25.0 ± 2.5 | 0.898 |
| Anion Gap (mmol/L) | 10-20 | 13.8 ± 5.4 | 12.0 ± 4.2 | 0.38 | 13.2 ± 6.3 | 13.2 ± 4.5 | 0.983 |

6. Evaluation of Lipid Metabolism after Administration of Enavogliflozin

Blood cholesterol was measured to confirm the effect of enavogliflozin on lipid metabolism. Changes in triglycerides and total cholesterol (T-Chol) were not statistically significant. Lipase also showed no significant difference before and after administration (Table 5). In Table 5, all values are expressed as mean±S.D, and p-values less than 0.05 were considered statistically significant.

TABLE 5

| | Reference | TOD test group (n = 10) | | | SID test group (n = 8) | | |
|---|---|---|---|---|---|---|---|
| Parameter | range | basal | treatment | p-value | basal | treatment | p-value |
| T-Chol (mg/dL) | 127-340 | 377.5 ± 159.6 | 327.6 ± 114.7 | 0.414 | 351.8 ± 230.7 | 261.3 ± 150.5 | 0.058 |
| Triglyceride (mg/dL) | 21-116 | 529.7 ± 846.9 | 384.9 ± 425.3 | 0.308 | 417.8 ± 852.8 | 515.2 ± 977.9 | 0.293 |
| Lipase (U/L) | 5-90 | 176.1 ± 145.2 | 197.3 ± 230.1 | 1 | 177.1 ± 121.6 | 226.8 ± 215.0 | 0.944 |

7. Evaluation of Regulation of Blood Glucose after Administration of Enavogliflozin The regulation of blood glucose before and after administration was confirmed through blood tests (fructosamine and fasting glucose) and the daily insulin dose. In the TOD test group, fasting blood glucose and the daily insulin dose decreased, but the difference was not statistically significant. However, fructosamine concentration was improved ($p=0.041$). Meanwhile, in the SID test group, fructosamine levels ranged from 475.3±107.6 to 393.1±122.9 μmol/L ($p=0.034$), fasting blood glucose ranged from 330.8±118.0 to 215.5±126.2 mg/dL ($p=0.0078$), and the daily insulin dose ranged from 2.0±0.8 to 1.5±0.5 units/kg/day ($p=029$), so that all indices were statistically significantly improved. In addition, as a result of comparing the difference between the test groups at 8 weeks, there was no significant difference in fasting blood glucose, fructosamine, and insulin reduction rate. However, there was a tendency towards a decrease in the SID test group taking enavogliflozin once a day compared to the TOD test group taking enavogliflozin once every 3 days (FIGS. 2A to 2C).

Furthermore, as a result of confirming the long-term effectiveness by administering enavogliflozin at the same usage and dose for up to 6 months, fasting blood glucose, fructosamine and insulin reduction rate were improved in all SID/TOD test groups. Specifically, the SID administration group showed a statistically significant reduction in fasting blood glucose ($p<0.0234$) and insulin reduction rate ($p<0.0234$) (FIGS. 3A and 3C), and the TOD test group showed a statistically significant reduction in fructosamine ($p<0.0313$) (FIG. 3B).

CONCLUSION

In the present invention, 8 weeks of co-administration of enavogliflozin and insulin improved fructosamine concentrations and reduced insulin doses in type 1 diabetic dogs. Further, once-daily administration of enavogliflozin to diabetic dogs was effective for lowering systolic blood pressure. Six months of co-administration of enavogliflozin and insulin significantly reduced fasting blood glucose and insulin doses in type 1 diabetic dogs.

The results suggest that the combination therapy of an SGLT2 inhibitor enavogliflozin and insulin is more effective than insulin monotherapy in diabetic dogs in terms of blood glucose regulation. In addition, it was confirmed that taking enavogliflozin once a day reduced fructosamine and insulin doses more remarkably than taking enavogliflozin once every three days.

The invention claimed is:

1. A method for treating diabetes mellitus in an animal of the family Canidae, the method comprising administering enavogliflozin to an animal of the family Canidae in need of treatment, wherein the enavogliflozin is administered at a dose of 0.025 mg/kg once a day or once every three days.

2. The method of claim 1, wherein the diabetes mellitus is type 1 diabetes mellitus.

3. The method of claim 1, wherein the enavogliflozin is administered for at least 8 weeks.

4. The method of claim 1, wherein the enavogliflozin is administered for at least 6 months.

5. The method of claim 1, wherein the enavogliflozin reduces one or more indices selected from the group consisting of fructosamine, insulin dose, fasting blood glucose and systolic blood pressure.

6. The method of claim 1, wherein the diabetes mellitus is type 1 diabetes mellitus, and the enavogliflozin is administered in combination with a therapeutic agent for type 1 diabetes mellitus.

7. The method of claim 1, wherein the enavogliflozin is administered orally or parenterally.

8. The method of claim 1, wherein the animal of the family Canidae has a metabolic disorder selected from the group consisting of hyperglycemia, insulin deficiency and body weight loss.

9. The method of claim 1, wherein the enavogliflozin is administered in combination with insulin to an animal of the family Canidae.

* * * * *